Figure 1:
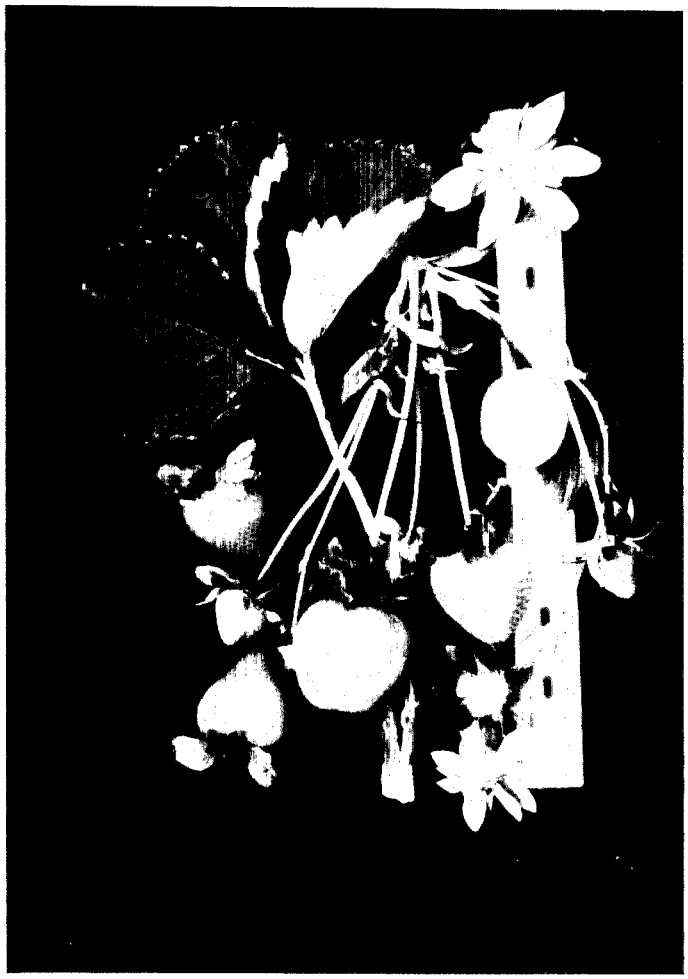

US00PP08649P

United States Patent [19]

Sjulin et al.

[11] Patent Number: Plant 8,649

[45] Date of Patent: Mar. 22, 1994

[54] STRAWBERRY PLANT CALLED 'KEY LARGO'

[75] Inventors: Thomas M. Sjulin, Watsonville; Amado Q. Amorao, Camarillo; Joseph I. Espejo, Jr., Watsonville, all of Calif.

[73] Assignee: Driscoll Strawberry Associates, Inc., Watsonville, Calif.

[21] Appl. No.: 26,312

[22] Filed: Mar. 2, 1993

[51] Int. Cl.[5] ..... A01H 5/00

[52] U.S. Cl. ..... Plt./48

[58] Field of Search ..... Plt. 48, 49

[56] References Cited

U.S. PATENT DOCUMENTS

P.P. 8,205 4/1993 Nelson et al. .

*Primary Examiner*—James R. Feyrer

*Attorney, Agent, or Firm*—Townsend and Townsend Khourie and Crew

[57] ABSTRACT

'UV601' is a spring bearing variety which produces attractive dark colored crown and main crop fruit from April to October when grown as a winter planted variety on the coast of central California and when adequately chilled before and after planting. The crop is early in maturing and in Florida ripens in December. 'UV601' has consistently firm skin and flesh, a large attractive calyx and good strawberry flavor. The variety is further characterized by its cordate-shaped leaflet serrations, acute at the apex, its purpling of leaf parts after the crown crop and its large calyx.

1 Drawing Sheet

DESCRIPTION

This invention relates to a new and distinct short day winter-planted spring bearing variety of strawberry plant named 'Key Largo' which is a result of a cross of Driscoll Strawberry Associates, Inc. non-patented selection "Z2" and Driscoll's variety 'Commander', U.S. Plant Pat. No. 7,024. The variety is botanically identified as *F.* ×*ananassa* Duch.

The seedlings resulting from the aforementioned cross were grown asexually multipled by stolon runners in Shasta County, Calif. Some plants of each seedling were held in Shasta County in a propagating nursery and other runner plants of each seedling clone were taken for testing to fruiting beds on the property of Driscoll Strawberry Associates, Inc. The runners from clones of the seedlings held in the Shasta County propagating nursery were set for further nursery propagation and for further testing at the fruiting beds. One plant was selected from the aforementioned group of seedlings and further asexually reproduced in the Shasta County nursery of Driscoll Strawberry Associates, Inc. Tests followed in various parts of California and Florida during intervening seasons on various properties of grower members of the Driscoll Strawberry Associates, Inc. These tests indicated the merits of 'Key Largo' and resulted in its selection as a promising test variety.

In the drawing, FIG. 1 shows plant parts of the new variety, typical in size, shape, and color.

The berry, known in cross section, illustrates flesh color and characteristic core cavity. The inflorescence illustrates typical branching and relative size about the middle of May. Long, strong pedicels holding both primary and secondary berries are shown. Two other picked berries illustrate the form and color of sepals and a flower with strong anther and pollen. A leaf with typical marginal leaflet serrations which are deep and have an acute apex is also shown. The underside of the leaflet is also illustrated. The leaflet has a typical petiolule and the leaflet blades are cupped upward. The primary berry attached to the inflorescence is typically wedge shaped in outline with slight longitudinal furrows and the two other individual berries are symmetrically conic with no furrows present which is more typical of secondary fruit.

The novel plant of 'Key Largo' is medium to large in size and is especially vigorous if given adequate chilling before being planted and give adequate nitrogen fertilizer. The plant, and especially leaflet margins, leaves and petioles become reddish purple after the main crop. This vegetative color is the color of the basal petiole bract shown in the drawing. The cause of this condition of the plant that is reflected in the reddish purpling of the plant is not understood, but it often seems to be correlated with poor plant vigor and it varies in intensity from one fruiting field to another. Extensive tests have been made to free 'Key Largo' of this anthocyanin pigmentation. At this time we have not correlated this coloring with a pathogen, including a virus, or a pest. If this condition is not severe, the plant of 'UV601' can become large, larger than 'Swede', the Driscoll variety, U.S. Plant Pat. No. 6,191. 'Key Largo' also produces more runners than 'Swede' during the fruiting season if given the same chilling before and after being planted. The winter planted 'Key Largo' is capable of producing fruit of good size and quality during its crown and first main crop. While 'Key Largo' is not an everbearer, it is capable of long season fruit production when grown in the central coast area of California. When dug at a high elevation nursery in northern California when the plants receive a minimum chilling before being dug and are given adequate cold-storage (33 degrees Fahrenheit) after being dug, long season production can be obtained. This gives a potential continuous production from late March to November if rain or cold temperatures do not prevent picking. If chilling exceeds these guidelines, excessive runners are produced with less fruit production and excessive plant growth. When grown in Florida, the plants usually receive less chilling before being dug at the nursery and are transplanted with some of the foliage present. These transplants with foliage present receive very little chilling before being transplanted and are capable of production for the fresh market from December through March. The early high quality fruit has an excellent shelf life and is especially valuable when produced in Florida and harvested during December and January. When transplanted from the nursery during mid-October, the first berries mature in Florida within 6 to 7 weeks of planting. The plant is capable of supporting this early crown crop, plus the first main crop, before foliage discoloration occurs. In the central coast areas of California where 'Key Largo' has been tested, the large attractive crown crop production is early, coming in mid-April, and is similar in yield and earliness to that of 'Swede'. The fruit is uniformly large and conic to slightly wedged with heavy shoulders and with a firm skin giving the fruit a good shelf life. The first main crop in central California comes in May and early June and produces fruit, including secondary and tertiaries, that are large, consistently dark, attractive in appearance and with a good flavor. Subsequent production produces fruit smaller in size with a greater drop in size between primaries and secondary fruit. The first main crop produces fruit large and attractive enough to be picked for "Long Stems" (a rating of 48 berries per single layer of a market crate), but subsequent berries don't maintain large enough size to qualify. Summer and fall production does continue, but 'Key Largo' produces poorly during mid-summer during some years and the berry size is smaller than that of 'Swede' and the Driscoll variety 'Commander', U.S. Plant Pat. No. 7,024. The total production of 'Key Largo', when grown at high elevation and planted in November in central California and measured in grams per plant, is near 'Swede' and slightly smaller in size when measuring grams per berry (Table 1). In Florida, when 'Key Largo' is compared to 'Oso Grande' (U.S. Plant Pat. No. 6,578) in production, 'Key Largo' starts with higher production and fruit size, but its total production is less and its average fruit size is only slightly larger (Table 1).

When comparing other physical characteristics of 'UV601' with 'Swede' and 'Commander', the plant of the new variety, when growing normally, is larger, lighter in color, and more rank in appearance than 'Swede' and often 'Commander', especially during the late spring and summer. The plant of 'Key Largo', when grown in central California after May and after February in Florida, often changes in appearance. This appearance change depends on the cultural practices, soil and climatic exposure it may receive, as will the cycling of the plant during the year. This change in the central coast of California seems to be correlated with a drop in the number of flowers initiated and subsequent less production. The plant becomes more vegetative and often more prostrate than 'Swede' whose cropping is more uniform in its production cycling. The plant shape appears more like 'Commander' in that it spreads its foliage more laterally in contrast to 'Swede' whose foliage is usually more erect than 'Commander' or 'Key Largo'. The petiole length is greater than 'Swede' (See Table 2). The canopy of 'Key Largo' also resembles 'Commander' rather than 'Swede' and is prone to be dense if given too much chilling before being planted. The leaflet margins of the new variety are distinct in that the serrations are deeper and the apex of individual serrations are more acute than the other two varieties. 'Key Largo' is distinct from 'Swede' and 'Commander' when observing their leaflet margins because of this serration difference, whether observing the upper or lower of the leaflets. Individual serrations are distinct on 'Key Largo' because of their deepness into the leaflet and the pointed tip of each serration. They don't become rounded as is usually the cases with 'Swede' or 'Commander' (see Table 2). The length of petioles during May and June are longer than 'Swede' and usually equal to 'Commander'. The leaflet surface of the new variety is not as rugose as 'Swede'. Bracts on petioles are usually as abundant as that produced by 'Swede' but may be less during the spring.

The overall inflorescence length, and the common peduncle length, of 'Key Largo' is longer than 'Swede'. This long inflorescence expalins why the fruit of 'Key Largo' often hangs low in the ditch, with most of its fruit exposed to sunlight in contrast to 'Swede' whose fruit matures closer to the crown. Individual pedicels holding primary berries is about the same in length, but not as thick as that of 'Swede'. This pedicel may originate at times mainly at the axil of a secondary peduncle, but at times from one of the secondary peduncles. 'Swede' originates its pedicel holding primary berries mostly at the axil of secondary peduncles. The new variety has hair held irregularly parallel to the pedicel of the tertiary fruit, in contrast to 'Swede' where the hair is perpendicular. The fruit shape of the 'Key Largo' is similar to 'Swede' in that both are short to medium conic to wedge in outline. The 'Swede' is even shorter conic or wedge as the season develops. 'Swede' is also more prone to producing primaries with longitudinal furrows and folds, and will actually split at the apex exposing the core of the berry. Primaries of 'Key Largo' produce berries with light furrows. 'Commander', produces longer fruit and even though it has most heavy shoulders, it will produce a percentage of shoulders that taper toward the calyx giving the fruit an almost necked appearance. This doesn't happen with 'Key Largo'. 'Key Largo' has a distinct uniform dark color with a strong skin, in contrast to 'Swede' that is prone to ripen unevenly with white shoulders if picked before complete ripening occurs and the skin of 'Swede' is not as firm as the new variety. The calyx of 'Key Largo' is large, even larger than that of 'Swede', with individual sepals that are also usually darker than that of 'Swede'.

'Key Largo' is susceptible to *Verticillium wilt,* the anthracnose disease caused by *Collectotrichum acutatum,* but it has not been severely susceptible to powdery mildew, Mycosphaerella leaf spot or angular leaf spot. Fruit of 'Key Largo' is less susceptible to postharvest decay by Botrytis and Rhizopus than 'Swede', but preharvest decay by Botrytis can occur under high moisture conditions. As a seedling and selection, it has withdstood, without noticeable injury, the natural infection of the known common virus components present in California. The plant is susceptible to injury from two-spotted spider mite as well as flower thrip. Flavor tests were conducted on 13 occasions in 1992 with an experienced panel of 6 to 17 individuals (median of 12 individuals), using coded samples. The flavor of 'Key Largo' was judged comparable to 'Swede' in all evaluations, and superior to 'Commander' in seven evaluations (Table 3). Refractometer readings indicate that fruit of 'Key Largo' has not given consistently higher percentages of soluble solids than 'Swede'.

The varietal characteristics of the novel plant described in detail were observed in May and June in Watsonville, Calif., which is near the Pacific Ocean. The measurements were made from plants planted in November and were dug at a high elevation nursery in October. Many characteristics such as crop, fruit size and shape, and plant size and color will vary during the summer and fall.

The color terminology is in accordance with the Munsell color system.

Plant: Medium to large if given ample chilling before planting, bcoming larger during summer, especially if plants do not become reddish purple as they mature. This reddish purple condition on petioles and leaflets is more prevalent on some soil types.

Leaves: Medium to large in size. Central leaflet is usually 7 to 10 cm in width and length with distinct serrations noticeable because of their abundance and their deepness and acute apex. Petiolules not long, 6 to 12 mm. Bracts may be present on petioles. Color of upper side of leaflet is 8.2GY3.2/6.1 to 9.3GY 3.0/6.8. Lower side 4.5GY-3.9/6.9.

Isozymes in leaf extract: Phosphoglucoisomerase (PGI) 3-banded Al. Leucine aminopephgase (LAP) 2-banded B3, Phosphoglucomutase (PGM) 2-banded C4. this testing was done by the Driscoll Strawberry Associates laboratory following the procedure described in the publication: Electrophoretic Characterization of California Strawberry Cultivars, by Bringhurst—1981 (see Table 4).

Runners: Runners are vigorous and considered abundant at the nursery and also in fruiting beds if given more than ideal chilling before or after being transplanted.

Inflorescence: Medium to long in length, mostly 25 to 35 cm, becoming longer in summer. The common peduncles are short to medium during May, mostly 5 to 13 cm in length. Pedicel holding primary berries medium to thick in diameter 2 to 3 mm and 7 to 11 cm in length. Pedicel holding primary berries may originate from an axil of secondary peduncles or on one of the peduncles. Primary and secondary berry may ripen at the same time on a given inflorescence. Hair on pedicels is irregularly parallel to the pedicel. Flowers are visible during the beginning of each new crop. Anthers produce an abundance of pollen even during early spring.

Fruit: The crown crop size is large and attractive, usually equal to or larger than those produced by the main crop. Primaries of main crop fruit are 40 to 50 mm in length with the width usually equal to the length. Primaries are mostly medium-conic to medium-wedge in outline with the secondary and tertiaries mostly symmetrically conic as illustrated in the U.S.D.A. Bulletin No. 1043. Most fruit surface is uniformly smooth except some primaries may have slight longitudinal furrows present. The shoulders are heavily rounded, not necked. The shape tends to be more irregular during summer production. The surface color maintains its uniform dark gloss, even after eastern shipments. The surface color is 6.3R-2.5/8.9 to 5.5R2.4/8.5 and the core color is 6.8R-3.7/15.8 from the surface to the core cavity. The core cavity becomes white. The skin surface is considered firm and the seeds are held equal to or slightly inserted. The seeds are abundant and are held noticeably close to each other on a given berry. The seeds are yellow but darken when exposed to sunlight.

Calyx: The calyx is noticeably large on all fruit, with the width of primaries 50–65 mm in diameter, 20 to 30% larger in diameter than the berry width. Tertiary berries also have a large calyx. Sepals mostly elliptical in outline, but can be cuneate, and overlap each other. Some sepals are serrated at their margins and are held irregularly clasping to the fruit but may be reflexed when fruit shoulders are large where sepals join the berry. The sepals are considered dark with the side facing the fruit, mostly 0.6G-2.8/6.5.

TABLE 1

1992 marketable fruit yield and size comparison of high elevation (McArthur, California) 'KeyLargo' compared to 'Swede' dug October 7, 1991 and planted November 6, 1991 in Watsonville, California.

MONTHLY YIELD IN GRAMS PER FLAT

| VARIETY | APR | MAY | JUN | JUL | AUG | SEP | OCT |
|---|---|---|---|---|---|---|---|
| 'KEY LARGO' | 115 | 226 | 253 | 208 | 314 | 314 | 106 |
| 'SWEDE' | 85 | 194 | 269 | 318 | 235 | 246 | 160 |

| VARIETY | TOTAL G/PL | SIZE G/FR |
|---|---|---|
| 'KEY LARGO' | 1433 | 25.2 |
| 'SWEDE' | 1508 | 26.2 |

1992.93 marketable fruit-yield and size comparison of high elevation (McArthur, California) 'Key Largo' compared to 'Oso Grande' dug as green plants and planted in Florida October 7, 1992.

| VARIETY | DEC | JAN | FEB | MAR | APR |
|---|---|---|---|---|---|
| 'KEY LARGO' | 141 | 179 | 93 | 348 | 182 |
| 'OSO GRANDE' | 122 | 187 | 326 | 359 | 220 |

| VARIETY | TOTAL G/PL | SIZE G/FR |
|---|---|---|
| 'KEY LARGO' | 943 | 22.2 |
| 'OSO GRANDE' | 1215 | 20.0 |

TABLE 2

Leaf Characteristics of 'Key Largo', 'Swede' and 'Commander' - Watsonville, California (July 13, 1993)

| | SERRATION DEPTH M.M.* | PETIOLE LENGTH C.M.** |
|---|---|---|
| 'KEY LARGO' | 5.12 | 18.8 |
| 'SWEDE' | 4.48 | 15.4 |
| 'COMMANDER' | 4.21 | 21.0 |

*= Measuring from serration apex to a line berween where serrations join.
**= Measuring from periolule to lowest point of basal bract.

TABLE 3

1992 FLY RANCH TIME OF PLANTING FLAVOR TEST SUMMARY

| EVAL DATE | RATE DATE | # OF EVAL. | LEVEL OF SIGN. | AVERAGE FLAVOR SCORE | |
|---|---|---|---|---|---|
| | | | | 7V258 | 'KEY LARGO' |
| 05/26/92 | 06/03/92 | 17 | 0.843 | 3.8 | 3.9 |
| 06/02/92 | 06/09/92 | 15 | 0.002** | 3.9 a | 3.3 bc |
| 06/16/92 | 06/24/92 | 12 | 0.002** | 3.8 a | 3.5 a |
| 06/30/92 | 07/01/92 | 16 | 0.000** | 3.5 a | 3.9 a |
| 06/24/92 | 07/02/92 | 12 | 0.072 | 3.8 | 3.7 |
| 07/07/92 | 07/15/92 | 12 | 0.494 | | 3.1 |
| 07/14/92 | 07/22/92 | 11 | 0.000** | | 3.0 b |
| 07/28/92 | 08/05/92 | 13 | 0.002** | 3.0 | 3.4 c |
| 08/04/92 | 08/12/92 | 11 | 0.061 | | |
| 08/11/92 | 08/19/92 | 7 | 0.234 | | |
| 08/18/92 | 08/27/92 | 10 | 0.000** | | 3.7 a |
| 08/25/92 | 09/02/92 | 6 | 0.194 | | 3.0 |
| 09/01/92 | 09/09/92 | 14 | 0.000** | | 3.7 a |
| 09/15/92 | 09/22/92 | 15 | 0.001** | | 3.4 a |
| 09/29/92 | 10/07/92 | 11 | 0.002** | | 3.5 ab |
| | | | AVERAGE: | 3.6 | 3.5 |

| | | | | 'COMMANDER' | 'SWEDE' |
|---|---|---|---|---|---|
| 05/26/92 | 06/03/92 | 17 | 0.843 | 3.6 | 3.8 |
| 06/02/92 | 06/09/92 | 15 | 0.002** | 3.1 c | 3.7 ab |
| 06/16/92 | 06/24/92 | 12 | 0.002** | 2.9 b | 3.7 a |
| 06/30/92 | 07/01/92 | 16 | 0.000** | 2.6 b | 3.5 a |
| 06/24/92 | 07/02/92 | 12 | 0.072 | 3.4 | 3.4 |

TABLE 3—continued

1992 FLY RANCH TIME OF PLANTING FLAVOR TEST SUMMARY

| EVAL DATE | RATE DATE | # OF EVAL. | LEVEL OF SIGN. | AVERAGE FLAVOR SCORE | |
|---|---|---|---|---|---|
| 07/07/92 | 07/15/92 | 12 | 0.494 | 3.5 | 3.3 |
| 07/14/92 | 07/22/92 | 11 | 0.000** | 2.3 c | 3.0 ab |
| 07/28/92 | 08/05/92 | 13 | 0.002** | 2.9 a | 2.8 a |
| 08/04/92 | 08/12/92 | 11 | 0.061 | 3.1 | 3.1 |
| 08/11/92 | 08/19/92 | 7 | 0.234 | 3.1 | 3.5 |
| 08/18/92 | 08/27/92 | 10 | 0.000** | 2.9 bc | 3.0 abc |
| 08/25/92 | 09/02/92 | 6 | 0.194 | 3.3 | 2.8 |
| 09/01/92 | 09/09/92 | 14 | 0.000** | 3.0 bc | 3.5 ab |
| 09/15/92 | 09/22/92 | 15 | 0.001** | 2.9 b | 3.5 a |
| 09/29/92 | 10/07/92 | 11 | 0.002** | 2.8 c | 4.0 a |

TABLE 3—continued

1992 FLY RANCH TIME OF PLANTING FLAVOR TEST SUMMARY

| EVAL DATE | RATE DATE | # OF EVAL. | LEVEL OF SIGN. | AVERAGE FLAVOR SCORE | |
|---|---|---|---|---|---|
| | | | AVERAGE: | 3.0 | 3.4 |

**Significantly different at or below the 1% level.

TABLE 4

'Key Largo' Isozyme banding patterns compared to 'Swede' and 'Commander' (July 8, 1993)

| CULTIVAR | PG1 | LAP | PGM |
|---|---|---|---|
| 'KEY LARGO' | A1 | B3 | C4 |
| 'SWEDE' | A1 | B3 | C2 |
| 'COMMANDER' | A4 | B3 | C4 |

F:PERFSOLDOCSO24269.1

We claim:

1. A new and distinct variety of strawberry plant described and illustrated and identified by the characteristics enumerated above.

* * * * *